(12) United States Patent
Matsuda et al.

(10) Patent No.: US 9,346,754 B2
(45) Date of Patent: May 24, 2016

(54) METHOD OF TREATING ADVANCED NON-ALCOHOLIC STEATOHEPATITIS

(71) Applicant: MediciNova, Inc., La Jolla, CA (US)

(72) Inventors: Kazuko Matsuda, Beverly Hills, CA (US); Yuichi Iwaki, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 14/490,618

(22) Filed: Sep. 18, 2014

(65) Prior Publication Data

US 2015/0322004 A1    Nov. 12, 2015

Related U.S. Application Data

(60) Provisional application No. 61/990,606, filed on May 8, 2014, provisional application No. 62/042,072, filed on Aug. 26, 2014.

(51) Int. Cl.
| | |
|---|---|
| *A61K 31/122* | (2006.01) |
| *A61K 31/05* | (2006.01) |
| *A61K 31/10* | (2006.01) |
| *C07C 323/22* | (2006.01) |

(52) U.S. Cl.
CPC ............. *C07C 323/22* (2013.01); *A61K 31/122* (2013.01); *A61K 31/05* (2013.01); *A61K 31/10* (2013.01)

(58) Field of Classification Search
CPC ...... A61K 31/122; A61K 31/05; A61K 31/10
See application file for complete search history.

(56) References Cited

U.S. PATENT DOCUMENTS

2005/0239902 A1* 10/2005 Locke et al. .................. 514/689

OTHER PUBLICATIONS

Ludwig et al. Mayo. Clin. Proc., 1980, vol. 55, Iss. 7, abstract.*
Pardee et al. Semin. Pediatr. Surg., 2009, vol. 18, No. 3, pp. 144-151.*
Hui et al., "Liver Fibrosis; Celecoxib potentiates experimental liver fibrosis," World Disease Weekly, Mar. 28, 2006, 2 pages.
Tian et al., "Selective COX-2 inhibitor celecoxib inhibits liver fibrogenesis in rats," Shijie Huaren Xiaohua Zazhi, 2011,19 (19), pp. 2002-2010 (with English Abstract).
Yu et al., "The anti-inflammatory effect of celecoxib does not prevent liver fibrosis in bile duct-ligated rats," Liver International, 2009, pp. 25-36.

* cited by examiner

*Primary Examiner* — Samira Jean-Louis
(74) *Attorney, Agent, or Firm* — Foley & Lardner LLP; Gilberto M. Villacorta; Lydia B. Choi

(57) ABSTRACT

A compound of Formula (I):

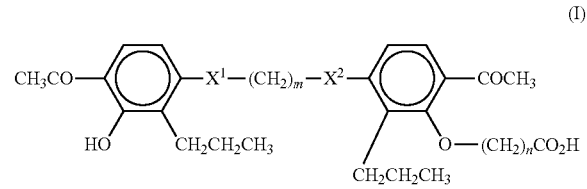

or a metabolite thereof, or an ester of the compound of Formula (I) or the metabolite thereof, or a pharmaceutically acceptable salt of each thereof, wherein m, n, $X^1$ and $X^2$ are as defined herein, is useful for inhibiting or treating advanced nonalcoholic steatohepatitis, conditions leading to or arising from it, and/or negative effects of each thereof.

30 Claims, 12 Drawing Sheets

FIG. 1A Photomicrographs Of HE-Stained Liver Sections
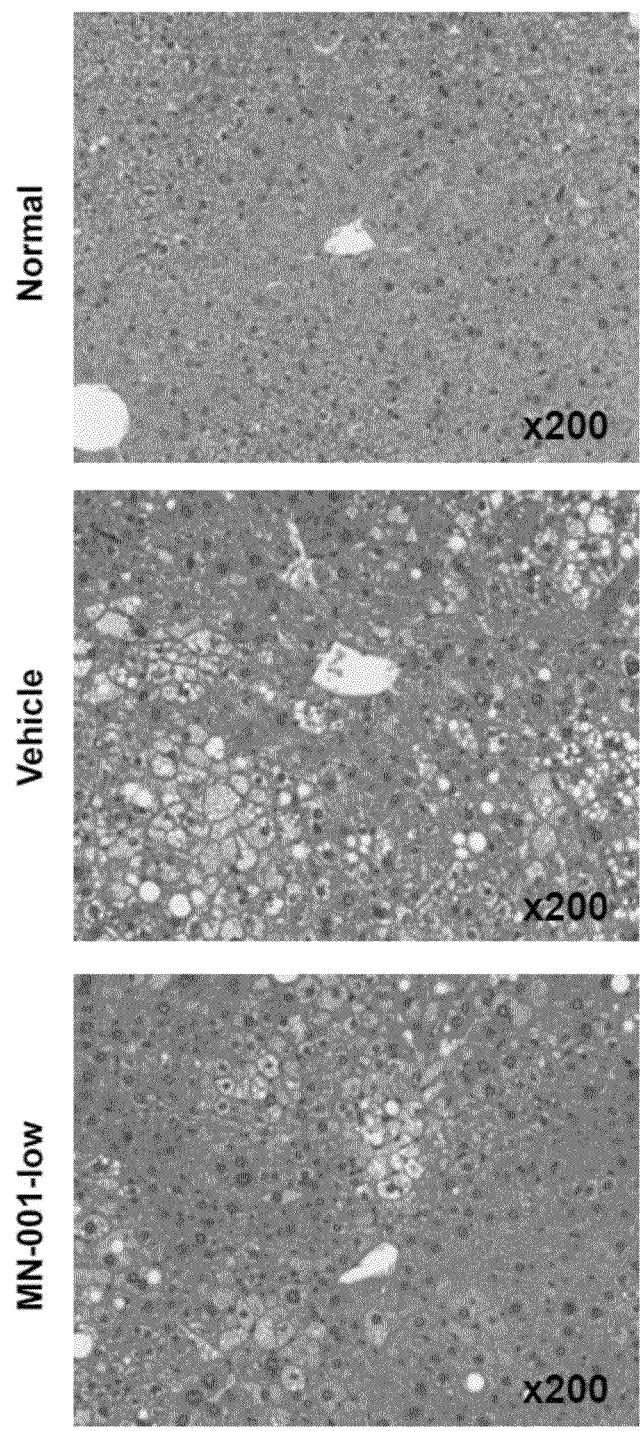

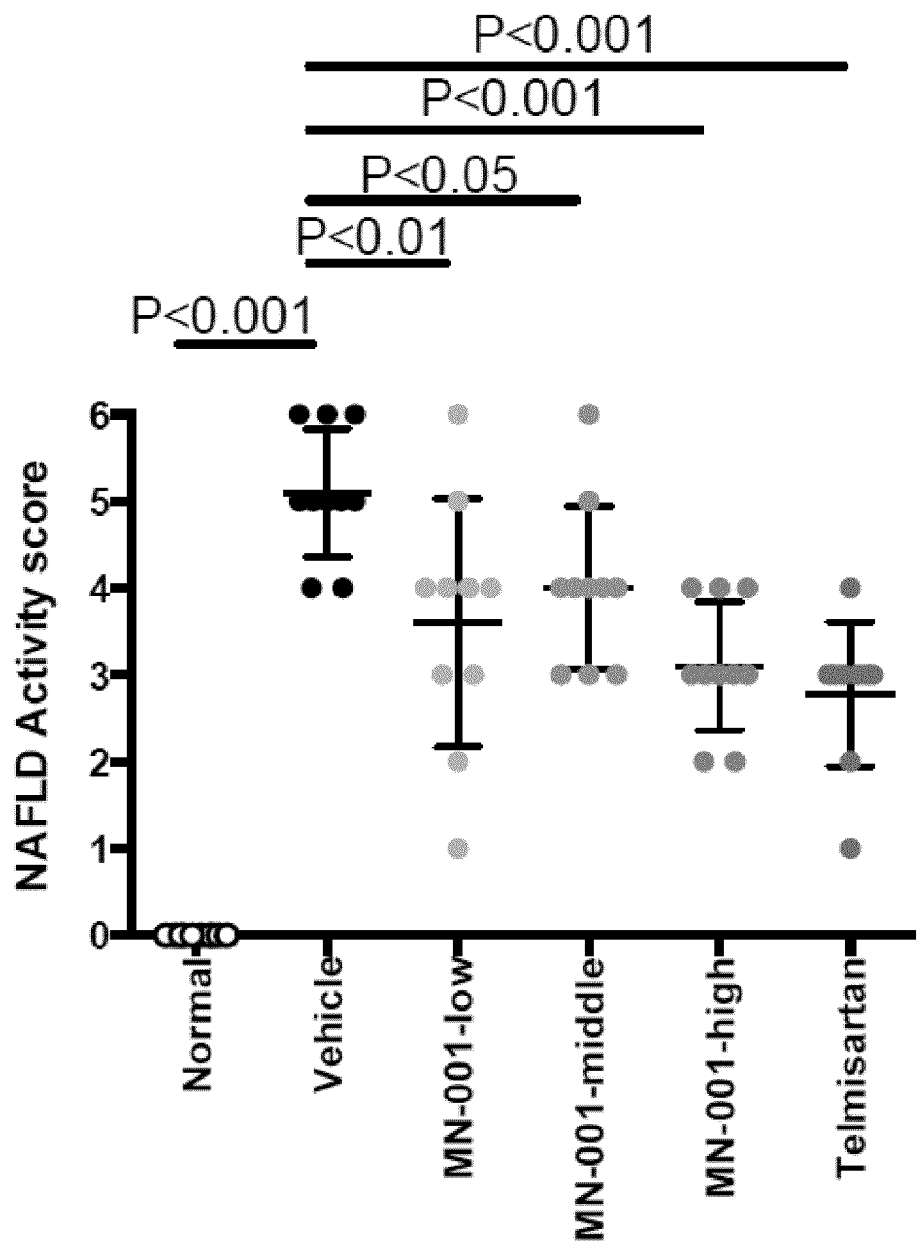
FIG. 2 NAFLD Activity Score

FIG. 3  Steatosis Score
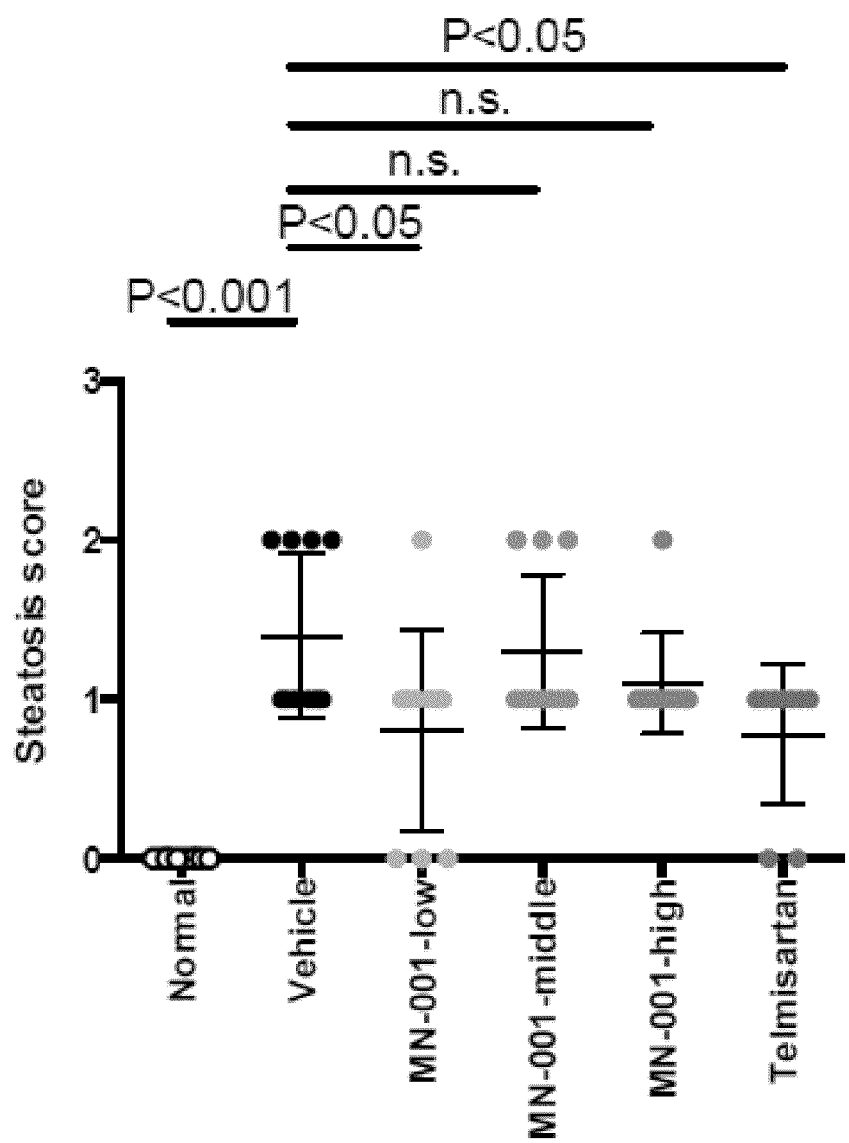

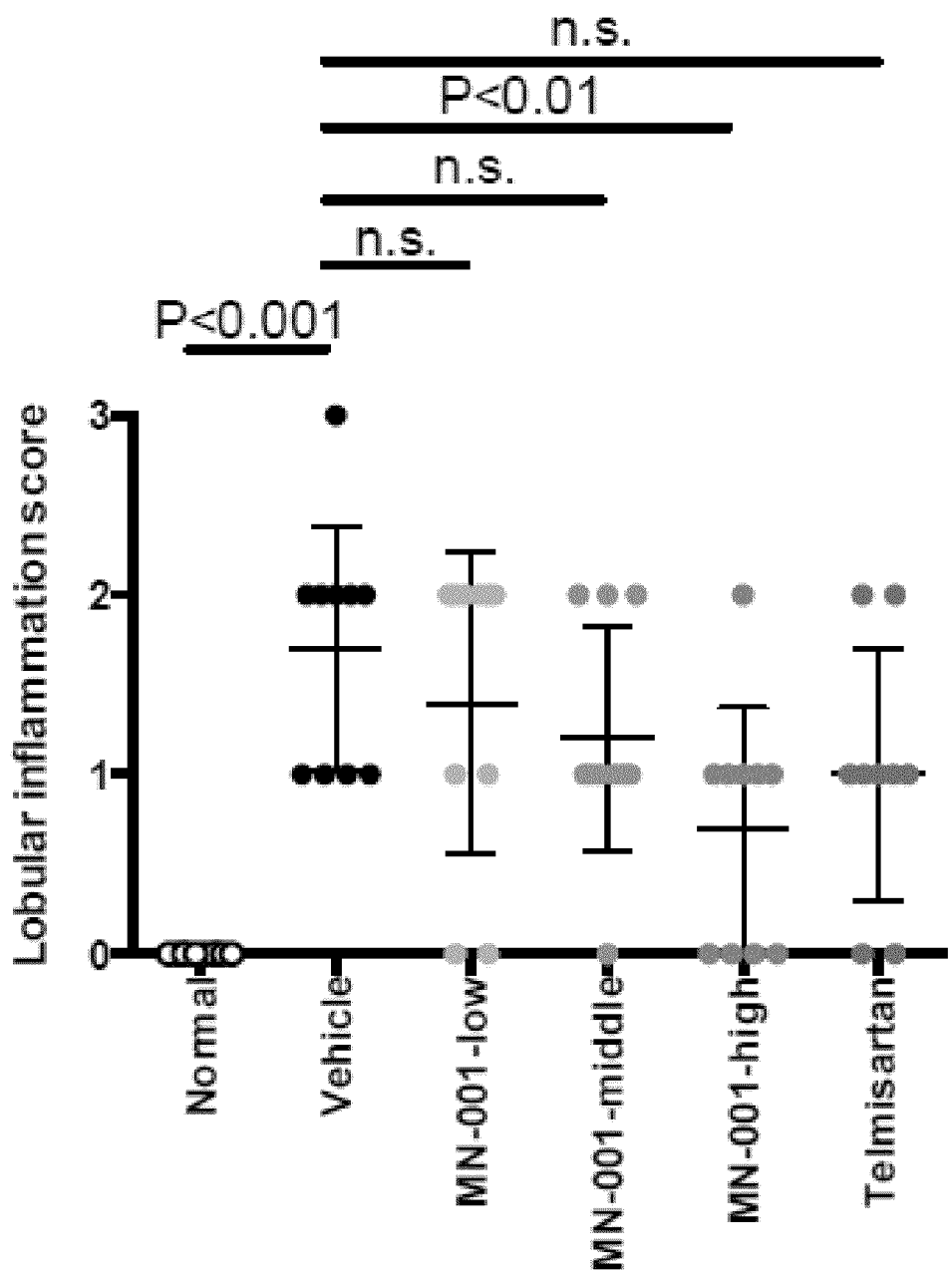
FIG. 4 Lobular Inflammation Score

FIG. 5  Hepatocyte Ballooning Score
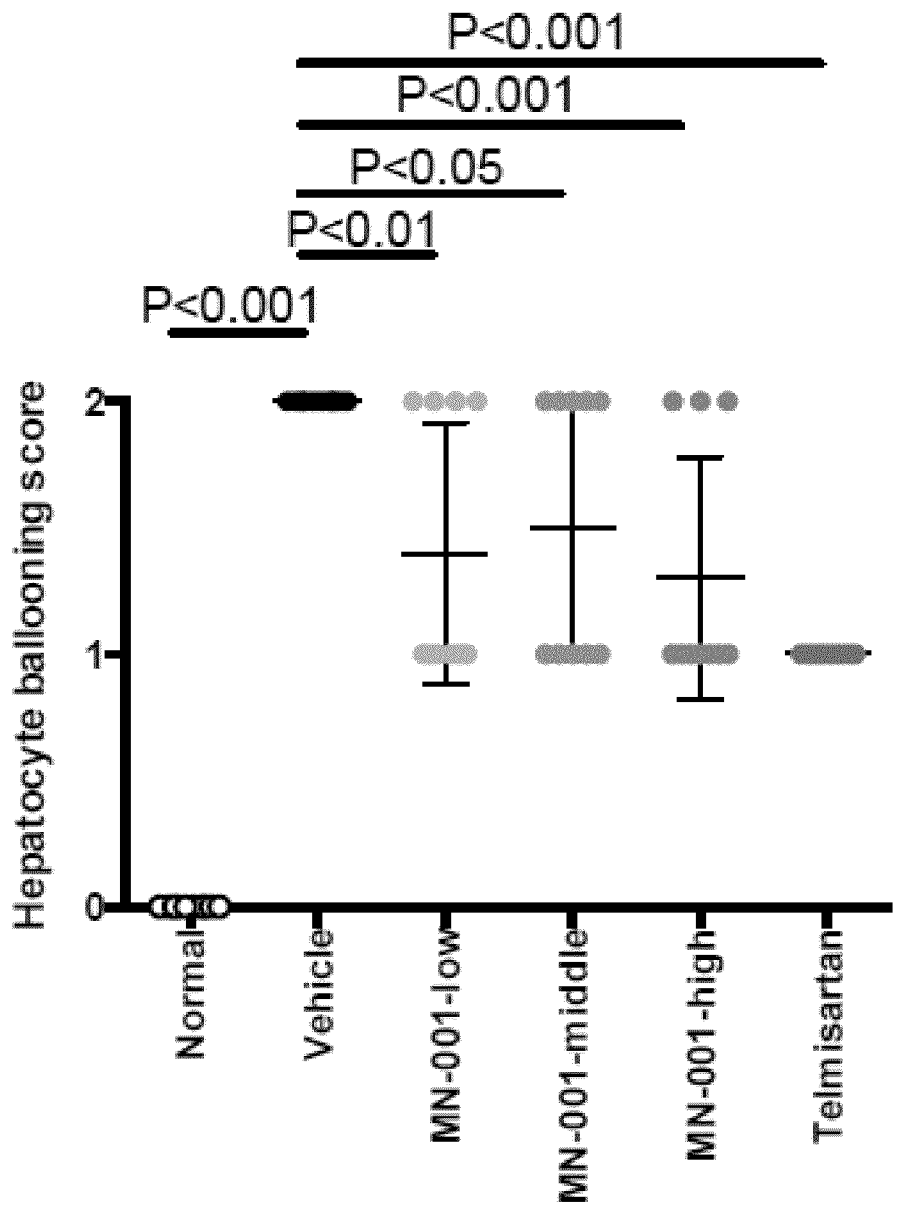

FIG. 6A Photomicrographs Of Sirius Red-Stained Liver Sections
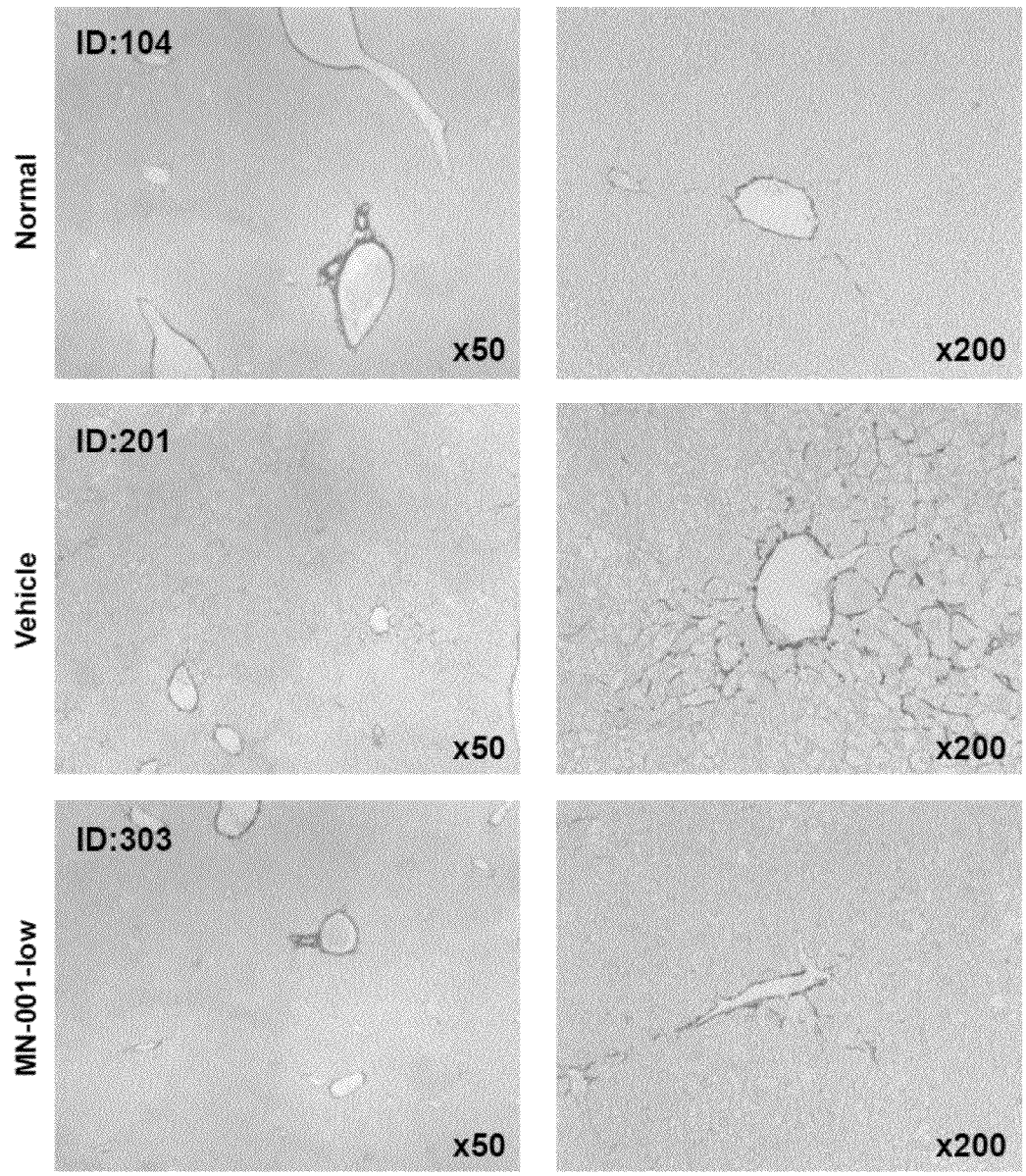

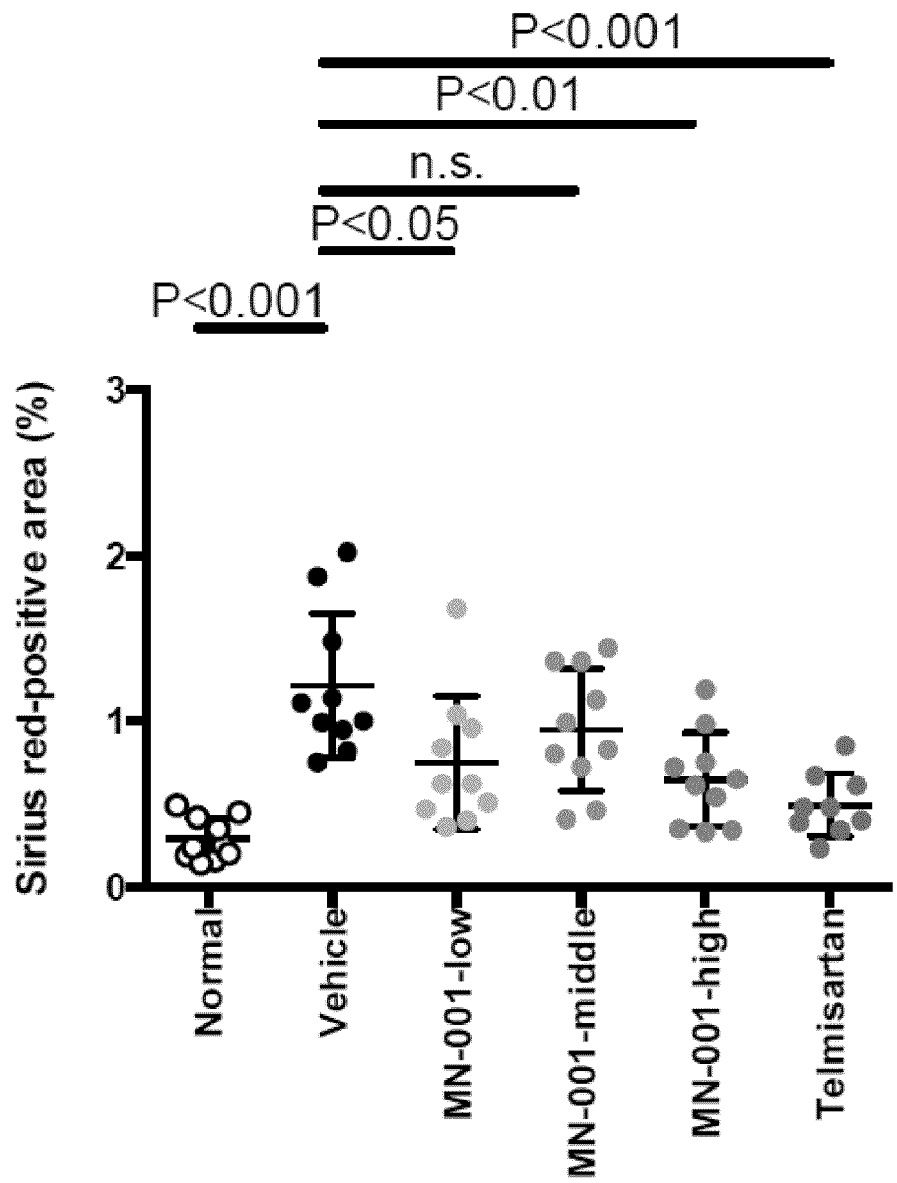
FIG. 7 Fibrosis Area

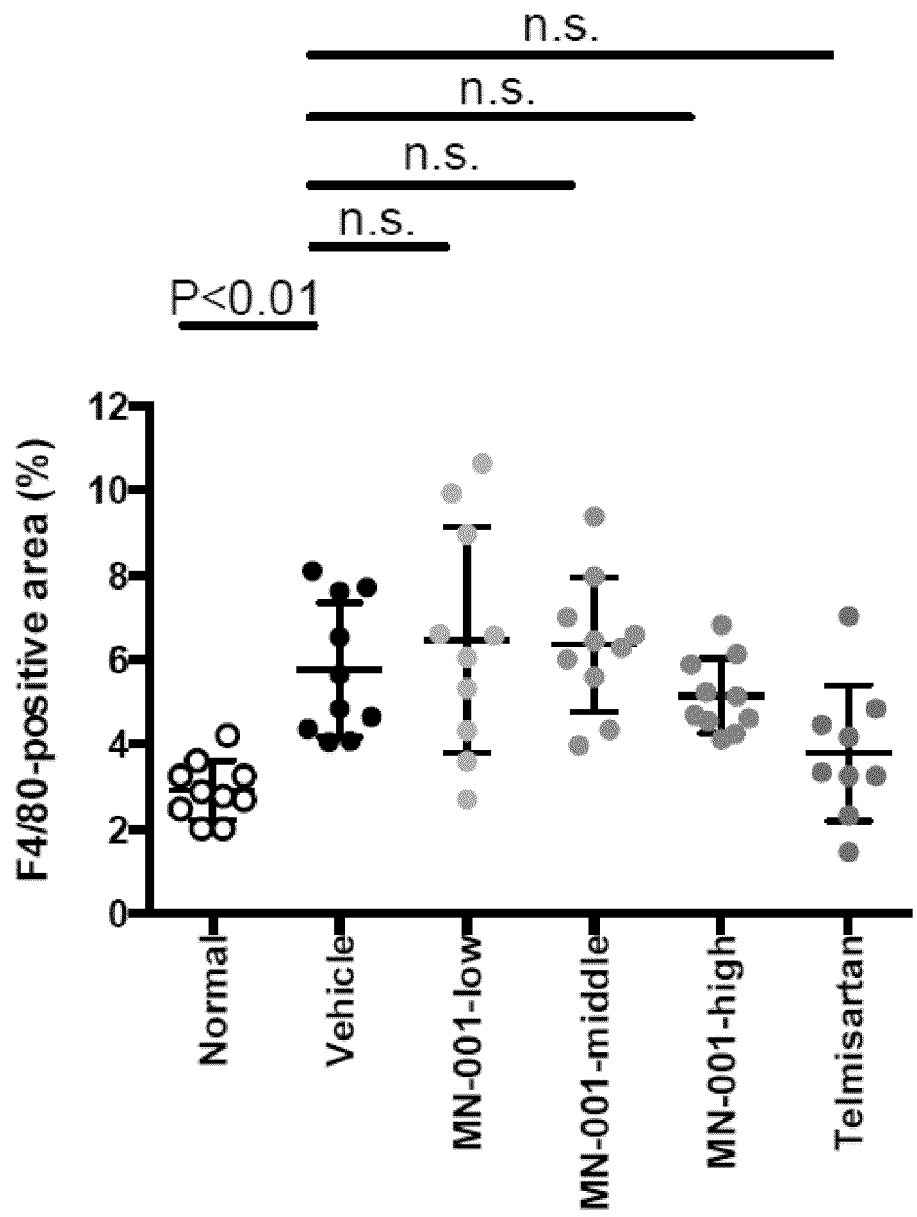
FIG. 8 Inflammation Area of Treated Liver

FIG. 9A Photomicrographs Of α-SMA-Immunostained Liver Sections
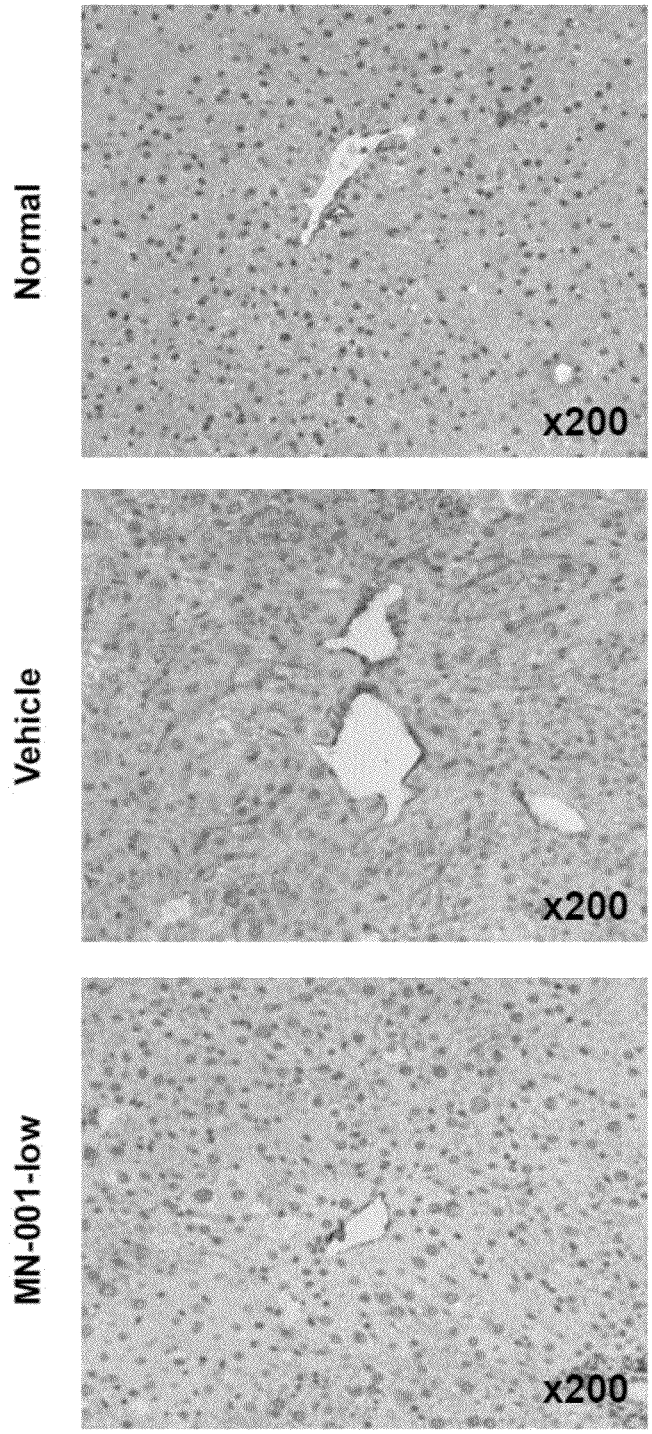

METHOD OF TREATING ADVANCED NON-ALCOHOLIC STEATOHEPATITIS

CROSS-REFERENCE TO RELATED APPLICATIONS

This application claims priority to U.S. provisional application No. 61/990,606, filed May 8, 2014, and U.S. provisional application No. 62/042,072 filed Aug. 26, 2014, each of which is incorporated herein in its entirety by reference.

FIELD

This technology relates to methods of inhibiting or treating advanced non-alcoholic steatohepatitis, conditions leading to or arising from it, and/or negative effects of each thereof by administering phenoxyalkylcarboxylic acids such as MN-001 and MN-002.

BACKGROUND

Non-alcoholic steatohepatitis or NASH is a common liver disease, which resembles alcoholic liver disease, but occurs in people who drink little or no alcohol. The major feature in NASH is fat in the liver, along with inflammation and damage. NASH can progress into advanced NASH, which is characterized, inter cilia, by hepatic fibrosis. Advanced NASH and conditions leading to or arising from advanced NASH, are a growing problem worldwide, affecting people of every age.

SUMMARY

The present disclosure provides a method of treating a patient diagnosed with advanced non-alcoholic steatohepatitis (NASH), the method comprising administering to the patient an effective amount of a compound of Formula (I), a metabolite of the compound of Formula (I), an ester of the compound of Formula (I), or a metabolite of the ester of the compound of Formula (I):

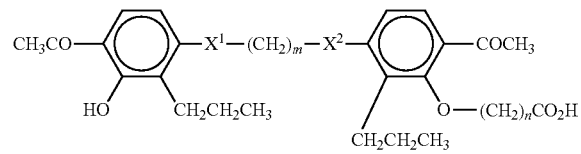

or a pharmaceutically acceptable salt of each of the foregoing, wherein m is an integer from 2 to 5 inclusive, and n is an integer from 3 to 8 inclusive, $X^1$ and $X^2$ each independently represent sulfur, oxygen, a sulfinyl group (—S(O)—) or a sulfonyl group (—S(O)$_2$—), provided that $X^1$ and $X^2$ are not simultaneously oxygen.

In a particular embodiment, the compound of Formula (I) is of Formula (IA):

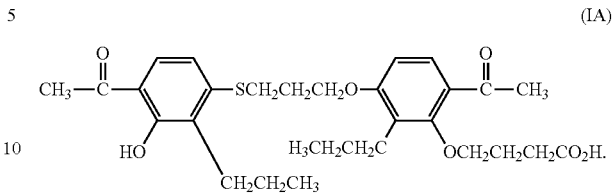

In another embodiment, the metabolite of the compound of Formula (I) is a compound of Formula (IB):

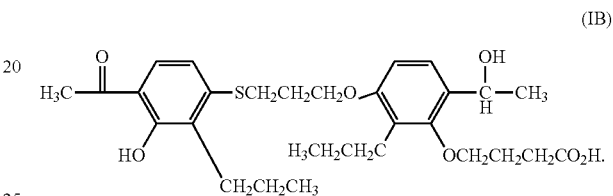

Preferably, the compound is administered orally, as a solid dosage form, such as a tablet or a capsule, and, more preferably, the compound is present in an orthorhombic crystalline form. The compound may also be administered as a liquid dosage form. The compound may be administered in an amount ranging from about 100 to about 4,000 mg/day, divided into one, two, or three portions.

In yet another embodiment the patient diagnosed with advanced NASH exhibits one or more of hepatic fibrosis, spider angiomata, ascites, splenomegaly, hard liver border, palmar erythema, asterixis, or portal hypertension. The patient may also exhibit one or more of hepatic scarring, cirrhosis, or hepatocellular carcinoma (HCC). In some instances the patient's hepatic fibrosis is reduced. In still other instances the patient's hepatic scarring is reduced. The patient may also be a pediatric patient, a juvenile patient, or an adult patient.

The present disclosure also provides a method of treating a patient diagnosed with advanced NASH, the method comprising administering to the patient an effective amount of a compound of Formula (IA), a metabolite of the compound of Formula (IA), an ester of the compound of Formula (IA), or a metabolite of the ester of the compound of Formula (IA):

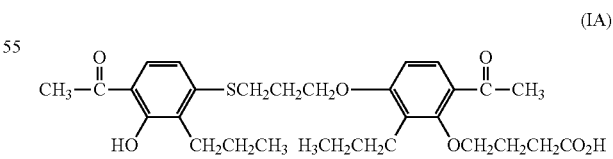

or a pharmaceutically acceptable salt of each of the foregoing.

Still another method provided is one of treating a patient diagnosed with advanced NASH, the method comprising administering to the patient an effective amount of a compound of Formula (IB), an ester of the compound of Formula (IB):

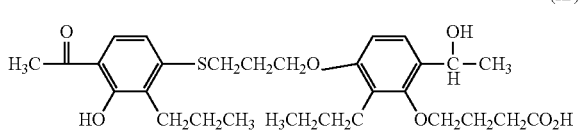

(IB)

or a pharmaceutically acceptable salt of each of the foregoing.

Still yet another method provided is one of treating a patient diagnosed with advanced NASH, the method comprising administering to the patient an effective amount of a compound of Formula (IA), a metabolite of the compound of Formula (IA), an ester of the compound of Formula (IA), a metabolite of the ester of the compound of Formula (IA):

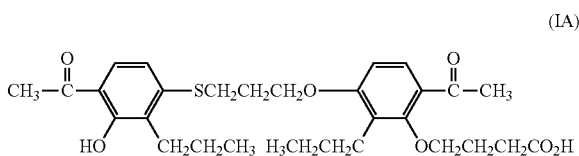

(IA)

or a pharmaceutically acceptable salt of each of the foregoing, wherein each of the foregoing is provided as a solid dosage form comprising orthorhombic crystals.

In another aspect, the present methods may reduce the likelihood of liver cirrhosis or hepatocellular carcinoma (HCC) in a patient suffering from advanced NASH, especially those exhibiting hepatic scarring.

BRIEF DESCRIPTION OF THE FIGURES

FIGS. 1A and 1B illustrate photomicrographs of HE-stained liver sections of treated and untreated mice.

FIG. 2 graphically illustrates NAFLD Activity Score (NAS) in treated and untreated mice FIG. 3 graphically illustrates steatosis scores in treated and untreated mice.

FIG. 4 graphically illustrates lobular inflammation scores in treated and untreated mice.

FIG. 5 graphically illustrates hepatocyte ballooning scores in treated and untreated mice.

FIGS. 6A and 6B illustrate photomicrographs of sirius red-stained liver sections of treated and untreated mice.

FIG. 7 graphically illustrates percentages of fibrosis area in treated and untreated mice.

FIG. 8 graphically illustrates inflammation area in treated and untreated mice.

FIGS. 9A and 9B illustrate photomicrographs of α-SMA-immunostained Liver Sections of treated and untreated mice.

DETAILED DESCRIPTION

Figure 1B:
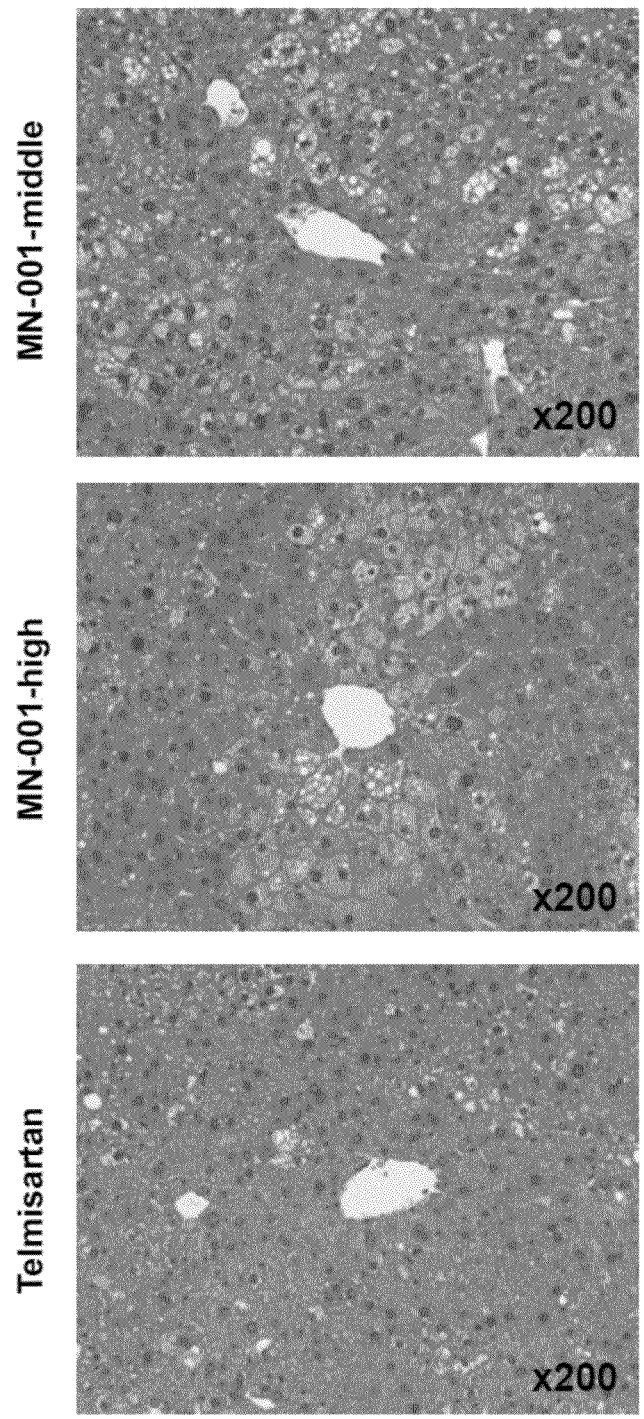

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

DEFINITIONS

As used herein, and in the appended claims, the singular forms "a," "an" and "the" include plural references unless the context clearly dictates otherwise.

"Administering" or "Administration of" a drug to a patient (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

"Advanced NASH" refers to a progression of NASH that leads to one or more symptoms such as spider angiomata, ascites, splenomegaly, hard liver border, palmar erythema, asterixis, hepatic fibrosis, and hepatocellular carcinoma. Advanced NASH is also associated with symptoms such as cirrhosis and liver failure, and with liver transplantation.

"$C_X$" when placed before a group refers to the number of carbon atoms in that group to be X.

"Alkyl" refers to a monovalent acyclic hydrocarbyl radical having 1 to 12 carbon atoms. Non limiting examples of alkyl include methyl, ethyl, propyl, isopropyl, butyl, isobutyl, tertiary butyl, pentyl, hexyl and the like.

"Aryl" refers to a monovalent aromatic hydrocarbyl radical having up to 10 carbon atoms. Non-limiting examples of aryl include phenyl and naphthyl.

"Heteroaryl" refers to an aromatic group of from 1 to 10 carbon atoms and 1 to 4 heteroatoms selected from the group consisting of oxygen, nitrogen, sulfur within the aromatic ring, wherein the nitrogen and/or sulfur atom(s) of the heteroaryl are optionally oxidized (e.g., N-oxide, —S(O)— or —S(O)$_2$—). Such heteroaryl groups can have a single ring (e.g., pyridyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. Non limiting examples of heteroaryl include pyridyl, pyrrolyl, indolyl, thiophenyl, and furyl.

"Cycloalkyl" refers to a monovalent non-aromatic cyclic hydrocarbyl radical having 3-12 carbon atoms. Non limiting examples of cycloalkyl include cyclopropyl, cyclobutyl, cyclopentyl, cyclohexyl, and the like.

"Heterocyclyl" refers to a monovalent non-aromatic cyclic group of 1 to 10 carbon atoms and 1 to 4 heteroatoms selected from the group consisting of oxygen, nitrogen, sulfur within the cycle, wherein the nitrogen and/or sulfur atom(s) of the heteroaryl are optionally oxidized (e.g., N-oxide, —S(O)— or —S(O)$_2$—). Such heteroaryl groups can have a single ring (e.g., piperidinyl or tetrahydrofuranyl) or multiple condensed rings wherein the condensed rings may or may not be aromatic and/or contain a heteroatom provided that the point of attachment is through an atom of the non-aromatic heterocyclyl group. Non limiting examples of heterocyclyl include pyrrolidinyl, piperidinyl, piperazinyl, and the like.

"Amino" refers to —NH$_2$.

"Alkylamino" refers to —NHR$_B$, wherein R$_B$ is C$_1$-C$_6$ alkyl optionally substituted with 1-3 aryl, heteroaryl, cycloalkyl, or heterocyclyl group.

"Dialkylamino" refers to —N(R$_B$)$_2$, wherein R$_B$ is defined as above.

"Comprising" shall mean that the methods and compositions include the recited elements, but not exclude others. "Consisting essentially of" when used to define methods and compositions, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transitional terms and phrases are within the scope of this invention.

"Effective amount" of a compound utilized herein is an amount that, when administered to a patient treated as herein, will have the intended therapeutic effect, e.g., alleviation, amelioration, palliation or elimination of one or more manifestations of the medical condition in the patient. The full therapeutic effect does not necessarily occur by administration of one dose (or dosage), and may occur only after administration of a series of doses. Thus, an effective amount may be administered in one or more administrations.

"Non-alcoholic steatohepatitis" or NASH is a common liver disease, which resembles alcoholic liver disease, but occurs in people who drink little or no alcohol. The major feature in NASH is fat in the liver, along with inflammation and damage. NASH can lead to cirrhosis, in which the liver is damaged, scarred, and is no longer able to work properly. NASH affects 2 to 5 percent of the U.S. population. Currently, no specific therapies for NASH exist. An additional 10 to 20 percent of Americans have fat in their liver, but no substantial inflammation or liver damage, a condition called "non-alcoholic fatty liver disease" (NAFLD). Although having fat in the liver is not normal, by itself it probably causes little harm or permanent damage. If fat is suspected based on blood test results or scans of the liver, this problem is referred to as NAFLD. If a liver biopsy is performed in this case, it will show that some people have NASH while others have NAFLD.

NASH is usually first suspected in a person who is found to have elevations in liver tests that are included in routine blood test panels, such as alanine aminotransferase (ALT) or aspartate aminotransferase (AST). When further evaluation shows no apparent reason for liver disease (such as medications, viral hepatitis, or excessive use of alcohol) and when x rays or imaging studies of the liver show fat, NASH is suspected. NASH is diagnosed and separated from NAFLD by a liver biopsy. For a liver biopsy, a needle is inserted through the skin to remove a small piece of the liver. NASH is diagnosed when examination of the tissue with a microscope shows fat along with inflammation and damage to liver cells. A biopsy can provide information about scar tissue has development in the liver.

NASH can but not always slowly worsen, developing to advanced NASH, causing scarring or fibrosis to appear and accumulate in the liver. As fibrosis worsens, cirrhosis may develop, and the liver becomes severely scarred, hardened, and unable to function normally. Once serious scarring or cirrhosis is present, few treatments can halt the progression. A person with cirrhosis can experience fluid retention, muscle wasting, bleeding from the intestines, and liver failure. Liver transplantation is the only treatment for advanced cirrhosis with liver failure, and transplantation is increasingly performed in people with advanced NASH. For example, NASH ranks as one of the major causes of cirrhosis in the U.S.A., along with hepatitis C and alcoholic liver disease.

Overall, morbidity and mortality have been shown to be significantly higher in NASH patients compared with the general population. Coronary artery disease and malignancy followed by liver-related mortality are the most common causes of death in NASH patients. Children with NASH also have a significantly shorter duration of survival compared with people in the general population.

Of patients with advanced NASH, 15% to 25% progress to cirrhosis and its complications over 10 to 20 years. At the time of initial biopsy, as many as one-third of NASH patients have advanced hepatic fibrosis, whereas 10% to 15% have well-established cirrhosis. It is now recognized that a large portion of patients with cryptogenic cirrhosis have burned-out NASH: the histologic feature of steatosis or steatohepatitis is replaced by a bland cirrhosis.

When cirrhosis appears, stigmata of chronic liver disease, such as spider angiomata, ascites, splenomegaly, hard liver border, palmar erythema, or asterixis, can be present. Patients can complain of jaundice or pruritus, or they might present with a complication of portal hypertension (e.g., ascites, variceal bleeding, or encephalopathy).

Cirrhosis in advanced NASH is a risk factor for development of hepatocellular carcinoma (HCC). A prevalence of HCC in up to 2.8% in NASH patients over a 20-year period has been reported. Data in Japanese patients report that the cumulative rate of HCC at 5 years may be as high as 15%. Advanced NASH-associated cirrhosis is an increasing indication for liver transplantation.

"Pharmaceutically acceptable" refers to non-toxic and suitable for administration to a patient, including a human patient.

"Pharmaceutically acceptable salts" refer to salts that are non-toxic and are suitable for administration to patients. Non-limiting examples include alkali metal, alkaline earth metal, and various primary, secondary, and tertiary ammonium salts. When the ester of the compound of Formula (I) includes a cationic portion, for example, when the ester includes an amino acid ester, the salts thereof can include various carboxylic acid, sulfonic acid, and miner acid salts. Certain non-limiting examples of salts include sodium, potassium, and calcium salts.

"Protecting groups" refer to well-known functional groups which, when bound to a functional group, render the resulting protected functional group inert to the reaction to be conducted on other portions of a compound and the corresponding reaction condition, and which can be reacted to regenerate the original functionality under deprotection conditions. The protecting group is selected to be compatible with the remainder of the molecule. A "carboxylic acid protecting group" protects the carboxylic functionality of the phenoxyalkylcarboxylic acids during their synthesis. Non limiting examples of carboxylic acid protecting groups include, benzyl, p-methoxybenzyl, p-nitrobenzyl, allyl, benzhydryl, and trityl. Additional examples of carboxylic acid protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting the carboxylic acids disclosed herein can be found in the art, and specifically in Greene and Wuts, supra, and the references cited therein.

"Treating" a medical condition or a patient refers to taking steps to obtain beneficial or desired results, including clinical results. For purposes of the various aspects and embodiments of the present invention, beneficial or desired clinical results include, but are not limited to, reduction, alleviation, or amelioration of one or more manifestations of or negative effects of advanced NASH, improvement in one or more clinical outcomes, diminishment of extent of advanced NASH, delay or slowing of advanced NASH progression, amelioration, palliation, or stabilization of the fibrosis state, and other beneficial results described herein.

Provided herein are methods administering an effective amount of a compound of Formula (I):

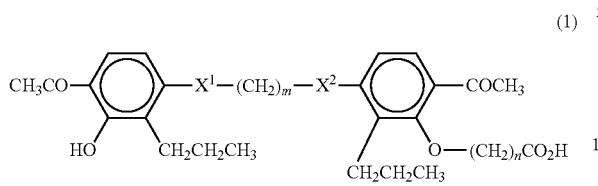

or a metabolite thereof, or an ester of the compound of Formula (I) or the metabolite thereof, or a pharmaceutically acceptable salt of each thereof, wherein the variables are defined as herein.

As used herein, "a metabolite thereof" refers to a metabolite that shows substantially similar therapeutic activity as a compound of Formula (I). Non limiting examples of such metabolites include compounds where the —COCH$_3$ group, of a compound of Formula (I), that is attached to the phenyl containing the —O—(CH$_2$)$_n$CO$_2$H moiety is metabolized to a 1-hydroxyethyl (—CH(OH)Me) group.

Metabolites containing such a 1-hydroxyethyl group contain an asymmetric center on the 1-position of the 1-hydroxyethyl group. The corresponding enantiomers and mixtures thereof, including racemic mixtures, are included within the metabolites of the compound of Formula (I) as utilized herein.

As used herein, "an ester thereof" refers to an ester of the phenolic hydroxy group and/or an ester of the carboxylic acid shown in the compound of Formula (I), and an ester of the 1-hydroxyethyl (an aliphatic hydroxy group) group of a metabolite of the compound Formula (I). An ester of the phenolic and/or the aliphatic hydroxy groups can include, without limitation, as the corresponding acid, a carboxylic acid R$_A$—CO$_2$H, wherein R$_A$ is C$_1$-C$_5$ alkyl, aryl, heteroaryl, C$_3$-C$_{12}$ cycloalkyl, or C$_2$-C$_8$ heterocyclyl, wherein the alkyl, aryl, heteroaryl, cycloalkyl, or heterocyclyl are optionally substituted with from 1 to 4 C$_1$-C$_3$ alkyl, aryl, CO$_2$H, amino, alkylamino, or dialkylamino groups. Other acids such as mono-, di-, or tri phosphoric acids are also contemplated. An ester of the carboxylic acid can include, without limitation, as the corresponding alcohol, a compound of formula R$_A$—OH, wherein R$_A$ is defined as above. In one embodiment, only the carboxylic acid in Formula (I) is esterified. In another embodiment, only the phenolic hydroxy group in Formula (I) is esterified. In another embodiment, R$_A$ is C$_1$-C$_4$ alkyl. As will be apparent to the skilled artisan, such esters act as prodrugs that are hydrolyzed in vivo to release the compound of Formula (I) or a salt thereof.

In an embodiment, the compound of Formula (I) is a compound of Formula (IA):

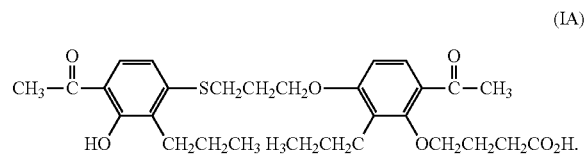

In another embodiment, the metabolite of the compound of Formula (I) and (IA) is a compound of Formula (IB):

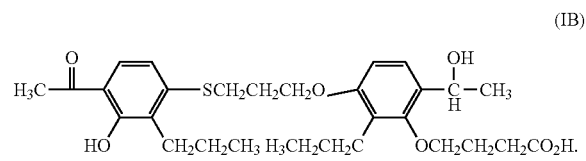

In another embodiment, the compound is administered orally. In another embodiment, the compound is administered as a tablet or a capsule. In another embodiment, the compound of Formula (IA) is present in polymorphic form A that is substantially free of other polymorphic forms. In another embodiment, the compound is administered as a liquid dosage form. In another embodiment, the compound is administered in an amount from about 100 to about 4,000 mg/day, divided into one, two, or three portions.

The efficacy of a compound utilized herein can be tested by methods well known to the skilled artisan, e.g., in a streptozocin induced model of advanced NASH and related liver conditions.

Synthesis

The synthesis and certain biological activity of the compounds of Formula (I) are described in U.S. Pat. No. 4,985,585 which is incorporated herein in its entirety by reference. For example, the compound of Formula (IA) is prepared by reacting a phenol of Formula (II):

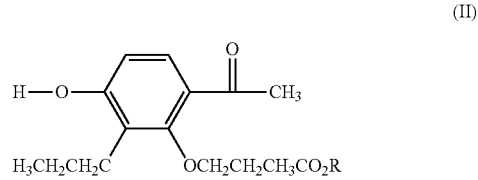

wherein, R is a carboxylic acid protecting group, with a compound of Formula (III):

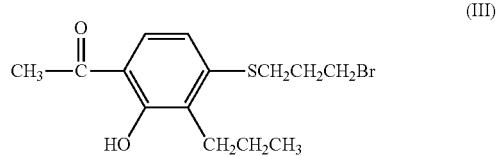

to provide a compound of Formula (IC):

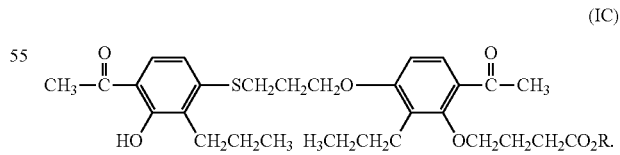

Non-limiting examples of acid protecting groups, or R groups, include C$_1$-C$_6$ alkyl, benzyl, benzhydryl, and trityl, wherein the benzyl, benzhydryl, or trityl group is optionally substituted with from 1 to 6 C$_1$-C$_6$ alkyl, halo, and/or C$_1$-C$_6$ alkoxy groups. It will be apparent to the skilled artisan that a leaving group other than the bromo group of Formula (III) may be used. Non-limiting examples of such other leaving groups include chloro or tosylate.

Deprotection of the protected carboxylic acid of Formula (IC) provides the compound of Formula (IA). As is apparent based on this disclosure, compounds of Formula (IC) are in some embodiments useful in accordance with this invention. Non-limiting examples of deprotection methods include, alkaline hydrolysis and hydrogenolysis under $H_2$ and a catalyst such as Pd/C or Pt/C.

The reactions are carried out in an inert organic solvent, for example and without limitation, acetone, methylethylketone, diethylketone, or dimethylformamide. The nucleophilic displacement reaction may be conducted at a temperature below room temperature up to the reflux temperature of the solvent, in the presence of an inorganic base, such as potassium carbonate or sodium carbonate, and optionally in the presence of potassium iodide. The reactions are carried out for a period of time sufficient to provide substantial product as determined by well-known methods such as thin layer chromatography and $^1$H-NMR. Other compounds utilized herein are made by following the procedures described herein and upon appropriate substitution of starting materials, and/or following methods well known to the skilled artisan. See also, U.S. Pat. No. 5,290,812 (incorporated herein in its entirety by reference).

The compound of Formula (IA) is recrystallized under controlled conditions to provide an essentially pure orthorhombic polymorph, referred to as Form A crystals (e.g., 90% or more, preferably at least 95% Form A). Polymorphic Form A and processes for producing it are described in U.S. Pat. Nos. 7,060,854 and 7,064,146; which are incorporated herein in their entirety by reference. All polymorphic forms of the compound of Formula (I) are active, but polymorphic Form A is preferred. Under certain conditions, the solubility and the bioavailability of this polymorph is superior to the other polymorphs and thus Form A may offer improved solid formulations or solid dosage forms.

Form A crystals can be obtained, For example, by dissolving the compound of Formula (IA) in 5 to 10 parts by weight of ethanol at 25° C. to 40° C. to give a yellow to orange solution. The ethanol solution is charged with 1 to 10 parts of water and agitated at 20° C. to 25° C. for about 15 to 60 minutes and then at 5° C. to 10° C. for an additional period of from 1 to 4 hours, preferably 2.0 to 3.0 hours, resulting in an off-white suspension. To this suspension is added 5 to 15 parts of water and the mixture is agitated at 5 to 10° C. for an additional from 1 to 4 hours, preferably 1.5 to 2.0 hours. A solid, white to off-white product is isolated by vacuum filtration and the filter cake is washed with water and dried in a vacuum at 25° C. to 40° C. for 12 to 24 hours.

For compounds utilized herein that exist in enantiomeric forms, such as certain metabolites of the compound of Formula (I) (for example, the compound of formula IB), the two enantiomers can be optically resolved. Such a resolution is performed, for example, and without limitation, by forming diastereomeric salt of a base such as (S)-(−)-1-(1-naphthyl)ethylamine with the corresponding carboxylic acid compound, or by separating the enantiomers using chiral column chromatography. Intermediates to such compounds, which intermediates also exist in enantiomeric forms can be similarly resolved.

Administration and Formulation

The compounds utilized herein can be administered orally, or by intravenous, intramuscular, and subcutaneous injection, or transdermal methods. Effective dosage levels can vary widely, e.g., from about 100 to about 4000 mg per day. In one embodiment, the daily dosage range is 250 to 2,000 mg, given in one, two or three portions. In one embodiment, the daily dosage range is 100 to 500 mg, such as 100, 200, 300, 400, or 500 mg given in one, two or three portions. In one embodiment, the daily dosage range is 250 to 2,000 mg, such as 250, 500, 750, 1,000, 1,250, 1,500, 1,750, or 2,000 mg given in one, two or three portions. In one embodiment, the daily dosage range is 1000 to 4,000 mg, such as 1,000, 2,000, 3,000, or 4,000 mg, given in one, two or three portions. In another embodiment, the dosage is 1000 mg twice a day. In other embodiments, suitable dosages include 1000 mg qd, 1000 mg bid, and 750 mg tid.

Actual amounts will depend on the circumstances of the patient being treated. As those skilled in the art recognize, many factors that modify the action of the active substance will be taken into account by the treating physician such as the age, body weight, sex, diet and condition of the patient, the time of administration, the rate and route of administration. Optimal dosages for a given set of conditions can be ascertained by those skilled in the art using conventional dosage determination tests.

The compounds utilized herein can be formulated in any pharmaceutically acceptable form, including liquids, powders, creams, emulsions, pills, troches, suppositories, suspensions, solutions, and the like. Therapeutic compositions containing the compounds utilized herein will ordinarily be formulated with one or more pharmaceutically acceptable ingredients in accordance with known and established practice. In general, tablets are formed utilizing a carrier such as modified starch, alone or in combination with carboxymethyl cellulose (Avicel), for example at about 10% by weight. The formulations are compressed at from 1,000 to 3,000 pounds pressure in the tablet forming process. The tablets preferably exhibit an average hardness of about 1.5 to 8.0 kp/cm$^2$, preferably 5.0 to 7.5 kp/cm$^2$. Disintegration time varies from about 30 seconds to about 15 or 20 minutes.

Formulations for oral use can be provided as hard gelatin capsules wherein the therapeutically active compounds utilized herein are mixed with an inert solid diluent such as calcium carbonate, calcium phosphate or kaolin, or as soft gelatin capsules in which the compounds are mixed with an oleaginous medium, e.g., liquid paraffin or olive oil. Suitable carriers include magnesium carbonate, magnesium stearate, talc, sugar, lactose, pectin, dextrin, starch, gelatin, tragacanth, methylcellulose, sodium carboxymethyl cellulose, a low melting wax, cocoa butter, and the like.

The compounds utilized herein can be formulated as aqueous suspensions in admixture with pharmaceutically acceptable excipients such as suspending agents, e.g., sodium carboxymethyl cellulose, methylcellulose, hydroxypropylmethyl cellulose, sodium alginate, polyvinylpyrrolidone, gum tragacanth and gum acacia; dispersing or wetting agents such as naturally occurring phosphatide, e.g., lecithin, or condensation products of an alkaline oxide with fatty acids, e.g., polyoxyethylene stearate, or condensation products of ethylene oxide with long chain aliphatic alcohols, e.g, heptadecaethylene-oxycetanol, or condensation products of ethylene oxide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monoleate. Such aqueous suspensions can also contain one or more preservatives, e.g., ethyl- or n-propyl-p-hydroxy benzoate, one or more coloring agents, one or more flavoring agents and one or more sweetening agents, such as glycerol, sorbitol, sucrose, saccharin or sodium or calcium cyclamate.

Suitable formulations also include sustained release dosage forms, such as those described in U.S. Pat. Nos. 4,788,055; 4,816,264; 4,828,836; 4,834,965; 4,834,985; 4,996,047;

5,071,646; and, 5,133,974, the contents of which are incorporated herein in their entirety by reference.

Other forms suitable for oral administration include liquid form preparations including emulsions, syrups, elixirs, aqueous solutions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Solid form preparations may contain, in addition to the active component, colorants, flavors, stabilizers, buffers, artificial and natural sweeteners, dispersants, thickeners, solubilizing agents, and the like.

The compounds utilized herein may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example as solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds utilized herein may be formulated for nasal administration. The solutions or suspensions are applied directly to the nasal cavity by conventional means, for example, with a dropper, pipette or spray. The formulations may be provided in a single or multidose form. The patient can administer an appropriate, predetermined volume of the solution or suspension via a dropper or pipette. A spray may be administered for example by means of a metering atomizing spray pump.

The compounds utilized herein may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine. The powder carrier will form a gel in the nasal cavity. The powder composition may be presented in unit dose form for example in capsules or cartridges of, for example gelatin or blister packs from which the powder may be administered by means of an inhaler.

The compounds utilized herein may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges including active agents in a flavored base, usually sucrose and acacia or tragacanth; pastilles including the active ingredient in an inert base such as gelatin and glycerin or sucrose and acacia; and mouthwashes including the active ingredient in a suitable liquid carrier.

The compounds utilized herein may be formulated for administration as suppositories. In such a formulation, a low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds utilized herein may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. A common type of controlled release formulation that may be used for the purposes of the present invention includes an inert core, such as a sugar sphere, a first layer, coated with an inner drug-containing second layer, and an outer membrane or third layer controlling drug release from the inner layer.

The cores are preferably of a water-soluble or swellable material, and may be any such material that is conventionally used as cores or any other pharmaceutically acceptable water-soluble or water-swellable material made into beads or pellets. The cores may be spheres of materials such as sucrose/starch (Sugar Spheres NF), sucrose crystals, or extruded and dried spheres typically includes excipients such as microcrystalline cellulose and lactose.

The substantially water-insoluble material in the first layer is generally a "GI insoluble" or "GI partially insoluble" film forming polymer (dispersed or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may include the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone, polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethyl hydroxyethyl cellulose, acrylic acid polymers, polymethacrylates, or any other pharmaceutically acceptable polymer. The ratio of drug to hydrophilic polymer in the second layer is usually in the range of from 1:100 to 100:1 (w/w).

Suitable polymers for use in the third layer, or membrane, for controlling the drug release may be selected from water insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above.

Optionally, the controlled release layer includes, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

Also provided herein are unit dosage forms of the formulations. In such forms, the formulation is subdivided into unit dosages containing appropriate quantities of the active component (e.g., and without limitation, a compound of Formula (I) or an ester thereof, or a salt of each thereof). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

The present invention, thus generally described, will be understood more readily by reference to the following examples, which are provided by way of illustration and are not intended to be limiting of the present invention.

EXAMPLES

The following abbreviations are used in the example and elsewhere in the application.
CCR: CC chemokine receptor
HE: Hematoxylin and eosin
HFD: High fat diet
MCP: Monocyte chemotactic protein
MMLV-RT: Molony murine leukemia virus reverse transcriptase
NAFLD: Non-alcoholic fatty liver disease
NAS: NAFLD Activity score
NASH: Non-alcoholic steatohepatitis
SD: Standard deviation
SMA: Smooth muscle actin
SPF: Specific pathogen-free
STAM: Stelic Animal Model
STZ: Streptozotocin
TIMP: Tissue inhibitor of metalloproteinase
FLAP: Five-lipoxygenase Activating Protein
LTC4: Leukotriene C4

Example 1

Treatment of Advanced NASH

Pathogen-free 15-day-pregnant C57BL/6 mice will be obtained from SLC-Japan, Inc. NASH will be established in male mice by a single subcutaneous injection of STZ (Sigma, USA) after birth and feeding with a high fat diet (HFD; CLEA-Japan, Japan) ad libitum after 4 weeks of age (day 28±2). Randomization of mice into 6 groups of 10 mice at 8 weeks of age (day 63±2), the day before the start of treatment. Individual body weight will be measured daily during the treatment period, survival, clinical signs and behavior of mice will be monitored daily.

The following study groups will be used.

Group 1 (Normal): Ten normal mice will be fed a normal diet ad libitum without any treatment until 12 weeks of age.

Group 2 (Vehicle): Ten NASH mice will be orally administered vehicle [0.3% CMC] in a volume of 10 mL/kg once daily from 8 to 12 weeks of age.

Group 3 (MN-001-low dose): Ten NASH mice will be orally administered vehicle supplemented with MN-001 at a dose of 10 mg/kg once daily from 8 to 12 weeks of age.

Group 4 (MN-001-middle dose): Ten NASH mice will be orally administered vehicle supplemented with MN-001 at a dose of 30 mg/kg once daily from 8 to 12 weeks of age.

Group 5 (MN-001-high dose): Ten NASH mice will be orally administered vehicle supplemented with MN-001 at a dose of 100 mg/kg once daily from 8 to 12 weeks of age.

Group 6 (Telmisartan): Ten NASH mice will be orally administered pure water supplemented with Telmisartan at a dose of 10 mg/kg once daily from 8 to 12 weeks of age.

Mice in all groups will be sacrificed for the following assays at 12 weeks of age. Individual liver weight will be measured, and liver-to-body weight ratio will be calculated. Liver hydroxyproline will be quantified by a hydrolysis method. Histopathological analyses of liver sections (according to routine methods) HE staining (to estimate NAFLD Activity score), Sirius-red staining (to estimate the percentage of fibrosis area). F4/80 immunostaining (to estimate the percentage of inflammation area), Alpha-SMA immunostaining (to estimate the percentage of a-SMA positive area) are performed. Gene expression assays using total RNA from the liver Real-time RT-PCR analysis will be performed for TIMP-1, Collagen Type 1, α-SMA, 5-lipoxygenase, FLAP and LTC4 synthase are also performed. Statistical tests will be performed using Bonferroni Multiple Comparison Test. P values<0.05 will be considered statistically significant.

Example 2

Treatment of Advanced NASH in Humans 250 adults with symptoms associated with advanced non-alcoholic steatohepatitis are randomly assigned to receive MN-001 or MN-002, each at a daily dose of 500 mg, or placebo, for up to 6 months. The primary outcome is an improvement in histologic features of nonalcoholic steatohepatitis, as assessed with the use of a composite of standardized scores for one or more of steatosis, lobular inflammation, hepatocellular ballooning, cirrhosis, and fibrosis. The results are analyzed following methods well known to the skilled artisan.

Example 3

Therapeutically Beneficial Effects of MN-001 in STAM Model of Advanced Non-Alcoholic Steatohepatitis STAM™ is a useful model for advanced non-alcoholic steatohepatitis (advanced NASH), symptoms thereof, and related liver disorders, created by the combination of chemical and dietary interventions in C57BL/6 mice. In this example, after inducing NASH, it was allowed to reach an advanced stage, and the mice were treated at 8-12 weeks. Telmisartan has been shown to have anti-NASH, -fibrosis and -inflammatory effects in STAN/1 mice and therefore was used as the positive control in the present study. According to this study, and as described below, treatment with Telmisartan significantly decreased liver weight, NAS, fibrosis area and inflammation area compared with the Vehicle group in agreement with reported data, thereby providing evidence of the usefulness of the STAM mice model as employed herein for demonstrating the usefulness of a compound utilized in this invention.

Treatment with high and middle doses of MN-001 significantly decreased NAFLD activity score (NAS). The improvement in NAS was attributable to the reduction in lobular inflammation and hepatocyte ballooning. Notably, high and middle doses of MN-001 significantly reduced ballooning score. The results demonstrate that MN-001 can improve advanced NASH pathology, e.g., and without limitation, by inhibiting hepatocyte damage and ballooning. As such, MN-001 showed anti-NASH and anti-fibrotic effects in advanced NASH stages.

Materials and Methods

Test Substance

To prepare dosing solutions, MN-001 was weighed and dissolved in 0.3% CMC (vehicle). Telmisartan (Micardis®) was purchased from Boehringer Ingelheim GmbH (Germany) and dissolved in pure water.

Inducing NASH

NASH was induced in 50 male mice by a single subcutaneous injection of 200 µg streptozotocin (STZ, Sigma-Aldrich, USA) solution 2 days after birth and feeding with high fat diet (HFD, 57 kcal % fat, cat#: HFD32, CLEA Japan, Japan) after 4 weeks of age.

Route of Drug Administration

Vehicle, MN-001, and Telmisartan were administered by oral route in a volume of 10 mL/kg.

Treatment Doses

MN-001 was administered at doses of 10, 30, and 100 mg/kg once daily. Telmisartan was administered at a dose of 10 mg/kg once daily.

Animals

C57BL/6 mice (15-day-pregnant female) were employed in the study.

Environment

The animals were maintained in a SPF facility under controlled conditions of temperature (23±2° C.), humidity (45±10%), lighting (12-hour artificial light and dark cycles; light from 8:00 to 20:00) and air exchange. A high pressure was maintained in the experimental room to prevent contamination of the facility.

Animal Husbandry

The animals were housed in polycarbonate cages KN-600 (Natsume Seisakusho, Japan) with a maximum of 4 mice per cage. Sterilized Paper-Clean (Japan SLC) was used for bedding and replaced once a week.

Food and Drink

Sterilized solid HFD was provided ad libitum, being placed in a metal lid on the top of the cage. Pure water was provided ad libitum from a water bottle equipped with a rubber stopper and a sipper tube. Water bottles were replaced once a week, cleaned and sterilized in autoclave and reused.

Animal and Cage Identification

Mice were identified by numbers engraved on earrings. Each cage was labeled with a specific identification code.

Measurement of Liver Biochemistry

Measurement of Liver Hydroxyproline Content

To quantify liver hydroxyproline content, frozen liver samples (32-40 mg) were processed by an alkaline-acid hydrolysis method as follows. Liver samples were defatted with 100% acetone, dried in the air, dissolved in 2N NaOH at 65° C., and autoclaved at 121° C. for 20 minutes. The lysed samples (400 µL) were acid-hydrolyzed with 400 µL of 6N HCl at 121° C. for 20 minutes, and neutralized with 400 µL of 4N NaOH containing 10 mg/mL activated carbon. AC buffer (2.2M acetic acid/0.48M citric acid, 400 µL) was added to the samples, followed by centrifugation to collect the supernatant. A standard curve of hydroxyproline was constructed with serial dilutions of trans-4-hydroxy-L-proline (Sigma-Aldrich) starting at 16 µg/mL. The prepared samples and standards (each 400 µL) were mixed with 400 µL chloramine T solution (Wako Pure Chemical Industries, Japan) and incubated for 25 minutes at room temperature. The samples were then mixed with Ehrlich's solution (400 µL) and heated at 65° C. for 20 minutes to develop the color. After samples were cooled on ice and centrifuged to remove precipitates, the optical density of each supernatant was measured at 560 nm. The concentrations of hydroxyproline were calculated from the hydroxyproline standard curve. Protein concentrations of liver samples were determined using a BCA protein assay kit (Thermo Fisher Scientific, USA) and used to normalize the calculated hydroxyproline values. Liver hydroxyproline levels were expressed as µg per mg protein.

Histopathological Analyses

For HE staining, sections were cut from paraffin blocks of liver tissue prefixed in Bouin's solution and stained with Lillie-Mayer's Hematoxylin (Muto Pure Chemicals, Japan) and eosin solution (Wako Pure Chemical Industries). NAFLD Activity score (NAS) was calculated according to the criteria of Kleiner (Kleiner D E. et al., *Hepatology*, 2005; 41:1313). To visualize collagen deposition, Bouin's fixed liver sections were stained using picro-Sirius red solution (Waldeck, Germany).

For immunohistochemistry, sections were cut from frozen liver tissues embedded in Tissue-Tek O.C.T. compound and fixed in acetone. Endogenous peroxidase activity was blocked using 0.03% H2O2 for 5 minutes, followed by incubation with Block Ace (Dainippon Sumitomo Pharma, Japan) for 10 minutes. The sections were incubated with a 200-fold dilution of anti-α-SMA (Epitomics, USA) or anti-F4/80 antibody (BMA Biomedicals, Switzerland) 1 hour at room temperature. After incubation with secondary antibody (HRP-Goat anti-rat antibody, Invitrogen, USA), enzyme-substrate reactions were performed using 3,3'-diaminobenzidine/H2O2 solution (Nichirei, Japan).

For quantitative analysis of fibrosis area, inflammation area, and semi-quantification of α-SMA, bright field images of Sirius red-stained, F4/80- and α-SMA-immunostained sections were captured around the central vein using a digital camera (DFC280: Leica Microsystems, Germany) at 200-fold magnification, and the positive areas in 5 fields/section were measured using ImageJ software (National Institute of Health, USA).

Quantitative RT-PCR

Total RNA was extracted from liver samples using RNAiso (Takara Bio, Japan) according to the manufacturer's instructions. One μg of RNA was reverse-transcribed using a reaction mixture containing 4.4 mM $MgCl_2$ (F. Hoffmann-La Roche, Switzerland), 40 U RNase inhibitor (Toyobo, Japan), 0.5 mM dNTP (Promega, USA), 6.28 μM random hexamer (Promega), 5× first strand buffer (Promega), 10 mM dithiothreitol (Invitrogen, USA) and 200 U MMLV-RT (Invitrogen) in a final volume of 20 μL. The reaction was carried out for 1 hour at 37° C., followed by 5 minutes at 99° C. Real-time PCR was performed using real-time PCR DICE and SYBR premix Taq (Takara Bio). To calculate the relative mRNA expression level, the expression of each gene was normalized to that of reference gene 36B4 (gene symbol: Rp1p0). Information of PCR-primer sets are described in Table 1.

TABLE 1

PCR primer Information

| gene | set ID | sequence |
|------|--------|----------|
| 36B4 | MA057856 | forward<br>5'-TTCCAGGCTTTGGGCATCA-3'<br>reverse<br>5'-ATGTTCAGCATGTTCAGCAGTGTG-3' |
| TIMP-1 | MA098519 | forward<br>5'-TGAGCCCTGCTCAGCAAAGA-3'<br>reverse<br>5'-GAGGACCTGATCCGTCCACAA-3' |
| Collagen Type 1 | MA075477 | forward<br>5'-CCAACAAGCATGTCTGGTTAGGAG-3'<br>reverse<br>5'-GCAATGCTGTTCTTGCAGTGGTA-3' |
| Alpha-SMA | MA057911 | forward<br>5'-AAGAGCATCCGACACTGCTGAC-3'<br>reverse<br>5'-AGCACAGCCTGAATAGCCACATAC-3' |
| 5-Lipoxygenase | MA148345 | forward<br>5'-TTGGCATCTAGGTGCAGTGTG-3'<br>reverse<br>5'-TGCGGAATCGGATCATGG-3' |
| FLAP | MA159311 | forward<br>5'-CGGACTGATGTACCTGTTTGTGAG-3'<br>reverse<br>5'-ATCCGCTTGCCGAAGATGTAG-3' |
| LTC4 synthase | MA085965 | forward<br>5'-CTGTGGCTGGCAACATGAAG-3'<br>reverse<br>5'-CCTTCGTGCAGAGATCACCTGTAG-3' |

Statistical Tests

Statistical analyses were performed using Bonferroni Multiple Comparison Test on GraphPad Prism 4 (GraphPad Software, USA). P values<0.05 were considered statistically significant. A trend or tendency was assumed when a one-tailed t-test returned P values<0.10. Results were expressed as mean±SD.

Experimental Design and Treatment

Study Groups

Group 1: Normal

Ten normal mice were fed with a normal diet ad libitum without any treatment until 12 weeks of age.

Group 2: Vehicle

Ten NASH mice were orally administered vehicle in a volume of 10 mL/kg once daily from 8 to 12 weeks of age.

Group 3: MN-001-Low Dose

Ten NASH mice were orally administered vehicle supplemented with MN-001 at a dose of 10 mg/kg once daily from 8 to 12 weeks of age.

Group 4: MN-001-Middle Dose

Ten NASH mice were orally administered vehicle supplemented with MN-001 at a dose of 30 mg/kg once daily from 8 to 12 weeks of age.

Group 5: MN-001-High Dose

Ten NASH mice were orally administered vehicle supplemented with MN-001 at a dose of 100 mg/kg once daily from 8 to 12 weeks of age.

Group 6: Telmisartan

Ten NASH mice were orally administered pure water supplemented with Telmisartan at a dose of 10 mg/kg once daily from 8 to 12 weeks of age.

Table 2 summarizes the treatment schedule.

TABLE 2

Treatment Schedule

| Group | No. mice | Mice | Test substance | Dose (mg/kg) | Volume (mL/kg) | Regimens | Sacrifice (wks) |
|-------|----------|------|----------------|--------------|----------------|----------|-----------------|
| 1 | 10 | Normal | — | — | — | — | 12 |
| 2 | 10 | STAM | Vehicle | — | 10 | Oral, once daily, 8 wks-12 wks | 12 |
| 3 | 10 | STAM | MN-001 | 10 | 10 | Oral, once daily, 8wks-12 wks | 12 |
| 4 | 10 | STAM | MN-001 | 30 | 10 | Oral, once daily, 8 wks-12 wks | 12 |
| 5 | 10 | STAM | MN-001 | 100 | 10 | Oral, once daily, 8 wks-12 wks | 12 |
| 6 | 10 | STAM | Telmisartan | 10 | 10 | Oral, once daily, 8 wks-12 wks | 12 |

Animal Monitoring and Sacrifice

The viability, clinical signs and behavior were monitored daily. Body weight was recorded before the treatment. Mice were observed for significant clinical signs of toxicity, moribundity and mortality approximately 60 minutes after each administration. The animals were sacrificed by exsanguination through direct cardiac puncture under ether anesthesia (Wako Pure Chemical Industries).

Results

Histological Analyses

HE Staining and NAFLD Activity Score (NAS)

NAFLD Activity Score (NAS) is a measure of the extent of liver damage, e.g., in a subject suffering from advanced NASH, and a damaged liver's response to treatment. Representative photomicrographs of the HE-stained sections are shown in FIGS. 1A and 1B. Liver sections from the Vehicle group exhibited severe micro- and macrovesicular fat deposition, hepatocellular ballooning and inflammatory cell infiltration. Consistent with these observations, NAS significantly increased in the Vehicle group compared with the Normal group. All doses of MN-001 treated groups showed marked improvements in hepatocellular ballooning and inflammatory cell infiltration. NAS were significantly decreased in all doses of the MN-001 treated groups compared with the Vehicle group. See, Tables 3 and 4 below, and FIGS. 2-5.

Sirius Red Staining

Figure 6B:
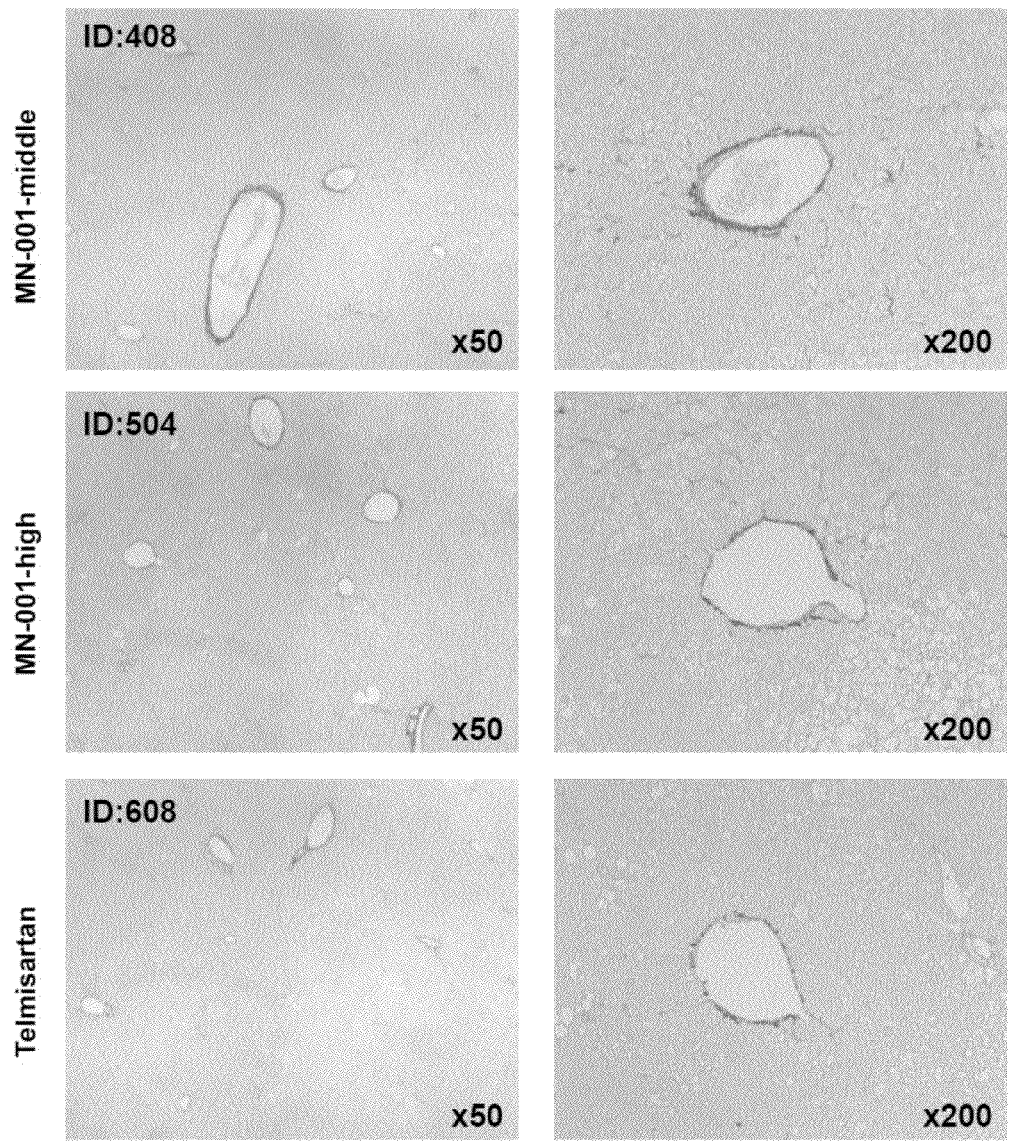

Representative photomicrographs of Sirius red-stained sections of livers are shown in FIGS. 6A and 6B. Liver sections from the Vehicle group showed increased collagen deposition in the pericentral region of liver lobule compared with the Normal group. The percentage of fibrosis area (Sirius red-positive area) significantly increased in the Vehicle group compared with the Normal group. The fibrosis area significantly decreased in the Telmisartan, MN-001-low and MN-001-high groups compared with the Vehicle group. The fibrosis area tended to decrease in the MN-001-middle dose group compared with the Vehicle group. See, Table 5 and FIG. 7.

F4/80 Immunostaining

Liver sections from the Vehicle group showed an increased number and size of F4/80-positive cells in the liver lobule compared with the Normal group. The percentage of inflammation area (F4/80-positive area) significantly increased in the Vehicle group compared with the Normal group. The inflammation area tended to decrease in the Telmisartan group. There were no significant differences in the inflammation area between the Vehicle group and any doses of the MN-001 treated groups, though an improvement was visible from FIG. 8. See also Table 5.

Alpha-SMA Immunostaining

Figure 9B:
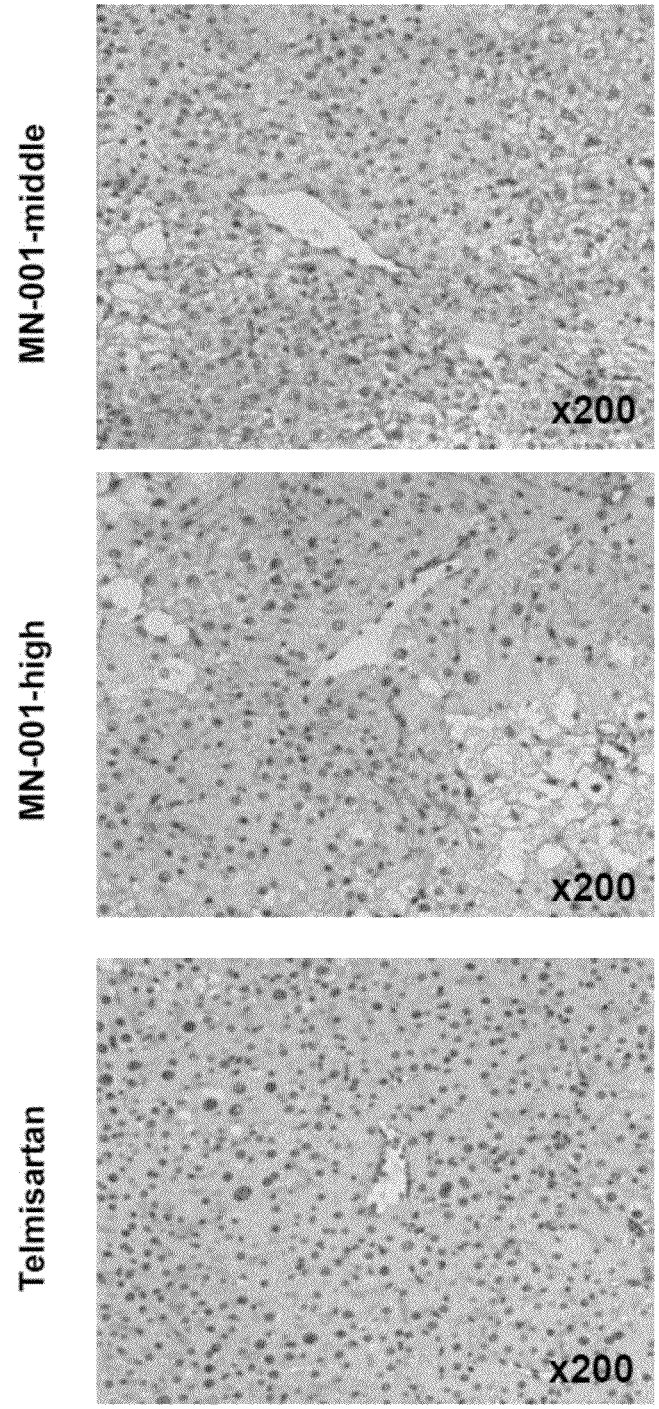

Representative photomicrographs of the α-SMA-immunostained sections are shown in FIGS. 9A and 9B. Liver sections from the Vehicle group showed an increased the number of α-SMA-positive cells in the liver lobule compared with the Normal group. The percentage of α-SMA-positive area significantly increased in the Vehicle group compared with the Normal group. The α-SMA-positive area significantly decreased in the Telmisartan, MN-001-low and -high groups compared with the Vehicle group. There was no significant difference in α-SMA-positive area between the Vehicle group and the MN-001-middle group. See Table 5 and FIGS. 9A and 9B.

TABLE 3

Improvement of NAS and NAS Components by MN-001

| | | | Score | | | | | | | |
|---|---|---|---|---|---|---|---|---|---|---|
| | | | | Lobular inflammation | | | | Hepatocyte ballooning | | |
| Group | n | Steatosis | 0 | 1 | 2 | 3 | 0 | 1 | 2 | NAS |
| Normal | 10 | 10 | — | — | — | 10 | — | — | — | 0.0 ± 0.0 |
| Vehicle | 10 | — | 6 | 4 | — | — | 4 | 5 | 1 | — | — | 10 | 5.1 ± 0.7 |
| MN-001-low | 10 | 3 | 6 | 1 | — | 2 | 2 | 6 | — | — | 6 | 4 | 3.6 ± 1.4 |
| MN-001-middle | 10 | — | 7 | 3 | — | 1 | 6 | 3 | — | — | 5 | 5 | 4.0 ± 0.9 |
| MN-001-high | 10 | — | 9 | 1 | — | 4 | 5 | 1 | — | — | 7 | 3 | 3.1 ± 0.7 |
| Telmisartan | 9 | 2 | 7 | — | — | 2 | 5 | 2 | — | — | 9 | — | 2.8 ± 0.8 |

TABLE 4

Definiton of NAS Components

| Item | Score | Extent |
|---|---|---|
| Steatosis | 0 | <5% |
| | 1 | 5-33% |
| | 2 | >33-66% |
| | 3 | >66% |
| Hepatocyte Ballooning | 0 | None |
| | 1 | Few balloon cells |
| | 2 | Many cells/prominent ballooning |
| Lobular Inflammation | 0 | No foci |
| | 1 | <2 foci/200x |
| | 2 | 2-4 foci/200x |
| | 3 | >4 foci/200x |

TABLE 5

Histological Analyses

| (mean ± SD) | Parameter | | | | | |
|---|---|---|---|---|---|---|
| | Normal (n = 10) | Vehicle (n = 10) | MN-001-low (n = 10) | MN-001-middle (n = 10) | MN-001-high (n = 10) | Telmisartan (n = 9) |
| Sirius red-positive area (%) | 0.29 ± 0.13 | 1.21 ± 0.44 | 0.75 ± 0.40 | 0.95 ± 0.37 | 0.65 ± 0.28 | 0.49 ± 0.19 |
| F4/80-positive area (%) | 2.92 ± 0.70 | 5.76 ± 1.60 | 6.47 ± 2.67 | 6.36 ± 1.59 | 5.14 ± 0.89 | 3.79 ± 1.60 |
| Alpha-SMA-positive area (%) | 0.49 ± 0.12 | 0.85 ± 0.35 | 0.45 ± 0.11 | 0.76 ± 0.19 | 0.48 ± 0.21 | 0.35 ± 0.14 |

Gene Expression Analysis

TIMP-1

TIMP-1 mRNA expression levels were significantly up-regulated in the Vehicle group compared with the Normal group. TIMP-1 mRNA expression levels were significantly down-regulated in the MN-001-low and Telmisartan groups compared with the Vehicle group. There were no significant differences in TIMP-1 mRNA expression levels between the Vehicle group and any of the other groups.

Collagen Type 1

Collagen Type 1 mRNA expression levels were significantly up-regulated in the Vehicle group compared with the Normal group. Collagen Type 1 mRNA expression levels were significantly down-regulated in the Telmisartan group compared with the Vehicle group. The MN-001-high group tended to decrease in collagen Type 1 mRNA expression levels compared with the Vehicle group. There were no significant differences in collagen Type 1 mRNA expression levels between the Vehicle group and any of the other groups.

Alpha-SMA

Alpha-SMA mRNA expression levels were significantly up-regulated in the Vehicle group compared with the Normal group. Alpha-SMA mRNA expression levels were significantly down-regulated in the Telmisartan group compared with the Vehicle group. There were no significant differences in α-SMA mRNA expression levels between the Vehicle group and any doses of the MN-001 treated groups.

Five-Lipoxygenase

Five-Lipoxygenase mRNA expression levels tended to increase in the Vehicle group compared with the Normal group. Five-Lipoxygenase mRNA expression levels in the MN-001-high and Telmisartan groups tended to decrease compared with the Vehicle group. There were no significant differences in 5-Lipoxygenase mRNA expression levels between the Vehicle group and the MN-001-low and -middle groups.

FLAP

FLAP mRNA expression levels were significantly up-regulated in the Vehicle group compared with the Normal group. FLAP mRNA expression levels in the MN-001-high group tended to increase in compared with the Vehicle group. There were no significant differences in FLAP mRNA expression levels between the Vehicle group and any of the other groups.

LTC4 Synthase

LTC4 synthase mRNA expression levels in the Telmisartan group tended to decrease compared with the Vehicle group. There were no significant differences in LTC4 synthase mRNA expression levels between the Vehicle group and any of the other groups.

Body Weight Changes and General Condition

Body weight gradually increased during the treatment period in all the groups except the Telmisartan group. Mean body weight of the Vehicle group was lower than that of the Normal group throughout the treatment period. Mean body weight of the Telmisartan group was significantly lower than that of the Vehicle group from day 8 to day 28. There were no significant differences in mean body weight between the Vehicle group and any of doses of MN-001 treated groups during the treatment period. One of the Telmisartan group was found dead on day 24. None of the animals showed deterioration in general condition.

Body Weight on the Day of Sacrifice

The Vehicle group showed a significant decrease in mean body weight on the day of sacrifice compared with the Normal group. The Telmisartan group showed a significant decrease in mean body weight on the day of sacrifice compared with the Vehicle group. There were no significant differences in mean body weight on the day of sacrifice between the Vehicle group and any doses of the MN-001 treated groups.

Liver Weight and Liver-to-Body Weight Ratio

The Vehicle group showed a significant increase in mean liver weight compared with the Normal group. The Telmisartan group showed a significant decrease in mean liver weight compared with the Vehicle group. There were no significant differences in mean liver weight between the Vehicle group and any doses of the MN-001 treated groups.

The Vehicle group showed a significant increase in mean liver-to-body weight ratio compared with the Normal group. The Telmisartan group showed a significant decrease in mean liver-to-body weight ratio compared with the Vehicle group. There were no significant differences in mean liver-to-body weight ratio between the Vehicle group and any doses of the MN-001 treated groups.

Liver Biochemistry

Liver Hydroxyproline Content

The Vehicle group tended to increase in liver hydroxyproline content compared with the Normal group. There were no significant differences in liver hydroxyproline content between the Vehicle group and any of the other groups.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of treating a patient diagnosed with advanced non-alcoholic steatohepatitis (NASH), which is a progression of NASH, including fibrosis, the method comprising administering to the patient an effective amount of a compound of Formula (I), a metabolite of the compound of Formula (I), an ester of the compound of Formula (I), or a metabolite of the ester of the compound of Formula (I):

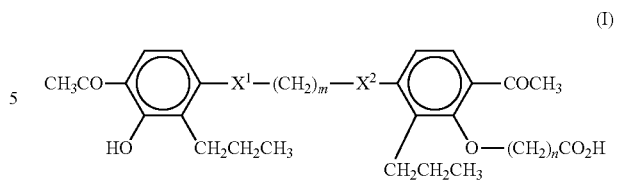

or a pharmaceutically acceptable salt of each of the foregoing, wherein m is an integer from 2 to 5 inclusive, and n is an integer from 3 to 8 inclusive, $X^1$ and $X^2$ each independently represent sulfur, oxygen, a sulfinyl group or a sulfonyl group, provided that $X^1$ and $X^2$ are not simultaneously oxygen.

2. The method of claim 1, wherein the compound of Formula (I) is of Formula (IA)

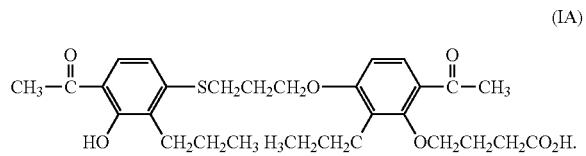

3. The method of claim 1, wherein the metabolite of the compound of Formula (I) is a compound of Formula (IB):

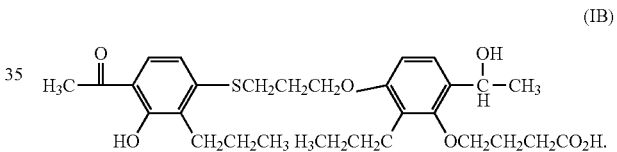

4. The method of claim 1, wherein the compound is administered orally.

5. The method of claim 4, wherein the compound is administered as a tablet or a capsule.

6. The method of claim 2, wherein the compound is present in an orthorhombic crystalline form.

7. The method of claim 1, wherein the compound is administered as a liquid dosage form.

8. The method of claim 1, wherein the compound is administered in an amount from about 100 to about 4,000 mg/day, divided into one, two, or three portions.

9. The method of claim 1, wherein the patient diagnosed with advanced NASH exhibits one or more of hepatic fibrosis, spider angiomata, ascites, splenomegaly, hard liver border, palmar erythema, asterixis, or portal hypertension.

10. The method of claim 9, wherein the patient's hepatic fibrosis is reduced.

11. The method of claim 1, wherein the patient diagnosed with advanced NASH exhibits one or more of hepatic scarring, cirrhosis, or hepatocellular carcinoma (HCC).

12. The method of claim 11, wherein the patient's hepatic scarring is reduced.

13. The method of claim 1, wherein the patient is a pediatric patient.

14. A method of treating a patient diagnosed with advanced NASH, which is a progression of NASH, including fibrosis, the method comprising administering to the patient an effective amount of a compound of Formula (IA), a metabolite of the compound of Formula (IA), an ester of the compound of Formula (IA), or a metabolite of the ester of the compound of Formula (IA):

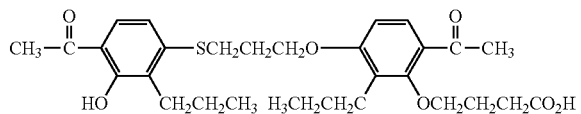
(IA)

or a pharmaceutically acceptable salt of each of the foregoing.

15. The method of claim 14, wherein the compound is administered orally.

16. The method of claim 14, wherein the compound is administered as a tablet or a capsule.

17. The method of claim 14, wherein the compound is administered as a liquid dosage form.

18. The method of claim 13, wherein the compound is administered in an amount from about 100 to about 4,000 mg/day, divided into one, two, or three portions.

19. The method of claim 14, wherein the patient diagnosed with advanced NASH exhibits one or more of hepatic fibrosis, spider angiomata, ascites, splenomegaly, hard liver border, palmar erythema, asterixis, or portal hypertension.

20. The method of claim 19, wherein the patient's hepatic fibrosis is reduced.

21. The method of claim 14, wherein the patient diagnosed with advanced NASH exhibits one or more of hepatic scarring, cirrhosis, or hepatocellular carcinoma (HCC).

22. The method of claim 21, wherein the patient's hepatic scarring is reduced.

23. A method of treating a patient diagnosed with advanced NASH, which is a progression of NASH, including fibrosis, the method comprising administering to the patient an effective amount of a compound of Formula (IB), an ester of the compound of Formula (IB):

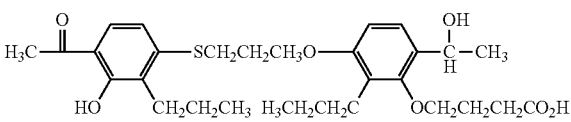
(IB)

or a pharmaceutically acceptable salt of each of the foregoing.

24. The method of claim 23, wherein the compound is administered orally.

25. A method of treating a patient diagnosed with advanced NASH, which is a progression of NASH, including fibrosis, the method comprising administering to the patient an effective amount of a compound of Formula (IA), a metabolite of the compound of Formula (IA), an ester of the compound of Formula (IA), a metabolite of the ester of the compound of Formula (IA):

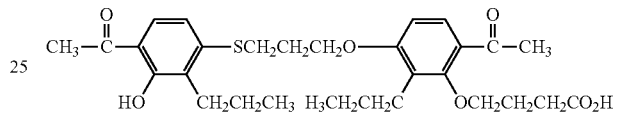
(IA)

or a pharmaceutically acceptable salt of each of the foregoing, wherein each of the foregoing is provided as a solid dosage form comprising orthorhombic crystals.

26. The method of claim 25, wherein the compound is administered in an amount from about 100 to about 4,000 mg/day, divided into one, two, or three portions.

27. The method of claim 24, wherein the patient diagnosed with advanced NASH exhibits one or more of hepatic fibrosis, spider angiomata, ascites, splenomegaly, hard liver border, palmar erythema, asterixis, or portal hypertension.

28. The method of claim 27, wherein the patient's hepatic fibrosis is reduced.

29. The method of claim 24, wherein the patient diagnosed with advanced NASH exhibits one or more of hepatic scarring, cirrhosis, or hepatocellular carcinoma (HCC).

30. The method of claim 29, wherein the patient's hepatic scarring is reduced.

* * * * *